(12) United States Patent
Chen

(10) Patent No.: US 8,864,495 B2
(45) Date of Patent: Oct. 21, 2014

(54) QUICK DENTAL IMPLANT KIT

(76) Inventor: Chun Chen, Taipei (TW)

( * ) Notice: Subject to any disclaimer, the term of this patent is extended or adjusted under 35 U.S.C. 154(b) by 0 days.

(21) Appl. No.: 13/420,022

(22) Filed: Mar. 14, 2012

(65) Prior Publication Data

US 2013/0244202 A1  Sep. 19, 2013

(51) Int. Cl.
*A61C 8/00* (2006.01)
*A61C 3/02* (2006.01)

(52) U.S. Cl.
USPC .......................................... 433/174; 433/165

(58) Field of Classification Search
USPC ............. 433/102, 165, 166; 606/80; 408/225, 408/228, 230
See application file for complete search history.

(56) References Cited

U.S. PATENT DOCUMENTS

| | | | | |
|---|---|---|---|---|
| 5,259,398 | A * | 11/1993 | Vrespa | 128/898 |
| 5,466,100 | A * | 11/1995 | Ahluwalia | 408/224 |
| 5,816,807 | A * | 10/1998 | Matsutani et al. | 433/165 |
| 5,839,897 | A * | 11/1998 | Bordes | 433/165 |
| 7,547,210 | B1 * | 6/2009 | Valen | 433/165 |
| 2008/0085488 | A1 * | 4/2008 | Lazarof | 433/50 |
| 2008/0280255 | A1 * | 11/2008 | D'Alise | 433/174 |
| 2009/0130631 | A1 * | 5/2009 | Chen | 433/174 |
| 2009/0258328 | A1 * | 10/2009 | Chen | 433/173 |
| 2009/0305189 | A1 * | 12/2009 | Scortecci et al. | 433/165 |
| 2010/0112517 | A1 * | 5/2010 | Chen | 433/165 |
| 2011/0033826 | A1 * | 2/2011 | Chen | 433/174 |

FOREIGN PATENT DOCUMENTS

WO   WO 2009/066935 A1 *  5/2009

* cited by examiner

*Primary Examiner* — Ralph Lewis
(74) *Attorney, Agent, or Firm* — Guice Patents PLLC

(57) ABSTRACT

A quick dental implant kit includes a fixture having an upper fine thread portion, a lower coarse thread portion and a diameter gradually reducing in direction from the top side toward the bottom side and exhibiting a long arc-shaped contour, and a drill bit having a shank connectable to and rotatable by a dental handpiece and a stepped cutter body formed integral with the bottom end of the shank and defining a plurality of stepped cutting edges for drilling a stepped hole in a jawbone of a patient for the implant of the fixture. Each stepped cutting edge defines at least five steps and at least four risers alternatively connected in a longitudinal series to fit the long arc-shaped contour of the fixture.

5 Claims, 10 Drawing Sheets

QUICK DENTAL IMPLANT KIT

BACKGROUND OF THE INVENTION

1. Field of the Invention

The present invention relates to dental implant technology and more particularly, to a quick dental implant kit, which uses a single drill bit configured subject to the contour of the fixture for drilling a stepped hole in the patient's jawbone for quick installation of the fixture.

2. Description of the Related Art

When a tooth wears out due to a poor dental care, or is damaged accidentally, and must be removed, a better method of treatment is to implant a suitable artificial tooth.

A dental implant surgery is to embed a screw shape fixture into the jawbone of the removed natural tooth, and then to fasten an abutment to the top side of the fixture with a screw after healing of the fixture and the jawbone, and then to install a crown in the abutment to complete the dental implant surgery.

However, after removal of the damaged natural tooth, it is necessary to drill a certain diameter of hole on the jawbone 100 before installation of the fixture P1, as shown in FIG. 2.

Further, a conventional method for drilling a hole in a jawbone for dental implant, shown in FIG. 1, is to drill a small hole in the jawbone 100 by using the smallest drill bit D1 of the smallest diameter d1, and then to drill the small hole into a drill hole 90 by using relatively greater drill bits D2~Dn of relatively greater diameters d2~dn in a proper order. The drill hole 90 has a diameter h slightly smaller than the diameter p of the fixture P1. After installation of the fixture P1 in the drill hole 90 in the jawbone 100, the threaded periphery of the fixture P1 can be tightly joined with the tissues of the jawbone 100.

The aforesaid conventional method for drilling a hole in a jawbone needs to use a set of drill bits D1~Dn of different diameters d1~dn. Thus, this multi-step method is complicated and time-consuming, and increases the patient's fear and the probability of a drill failure. Further, it is expensive to prepare a full set of different diameters of drill bits.

Therefore, it is desirable to provide a quick dental implant kit that eliminates the aforesaid problems.

SUMMARY OF THE INVENTION

The present invention has been accomplished under the circumstances in view. It is one object of the present invention to provide a quick dental implant kit, which facilitates quick drilling of a stepped hole in a jawbone for the implant of a fixture and saves much dental implant treatment time and labor.

To achieve this and other objects of the present invention, a quick dental implant kit comprises a fixture and a drill bit. The fixture comprises an upper fine thread portion disposed at the top side thereof and a lower coarse thread portion disposed at the bottom side thereof. The fixture has a diameter gradually reducing in direction from the top side toward the bottom side and exhibiting a long arc-shaped contour. The drill bit comprises a shank connectable to and rotatable by a dental handpiece, and a stepped cutter body formed integral with the bottom end of the shank and defining a plurality of stepped cutting edges for drilling a stepped hole in a jawbone of a patient for the implant of the fixture. Each stepped cutting edge defines at least five steps and at least four risers alternatively connected in a longitudinal series to fit the long arc-shaped contour of the fixture.

Further, the fixture comprises a plurality of spiral grooves located on the periphery and spirally extending from the top side of the lower coarse thread portion toward the bottom side thereof.

By means of using the drill bit configured to fit the contour of the fixture for drilling the desired stepped hole in the patient's jawbone instead of the prior art techniques of using a set of different diameters of drill bits, the invention greatly reduces the hole-drilling time, saves much the drill bit investment cost and shortens the treatment time.

Further, because each stepped cutting edge of the stepped cutter body of the drill bit defines at least five steps and at least four risers and the long arc-shaped contour of the fixture extends over the risers of each stepped cutting edge of the stepped cutter body of the drill bit, tissues in the stepped hole corresponding to the clearances between the at least five steps of the stepped cutter body of the drill bit and the long arc-shaped contour of the fixture are preserved, and these preserved tissues can be cut by the upper fine thread portion or lower coarse thread portion of the fixture and can fall into the spiral grooves upon installation of the fixture in the stepped hole. After the fixture has been completely embedded in the jawbone, the tissues in the jawbone are tightly abutted against the periphery of the fixture, and the cut tissue chips fill up the spiral grooves for cell proliferation, eliminating a further bone powder filling process and saving much dental implant treatment time and labor.

DETAILED DESCRIPTION OF THE PREFERRED EMBODIMENT

Figure 1:
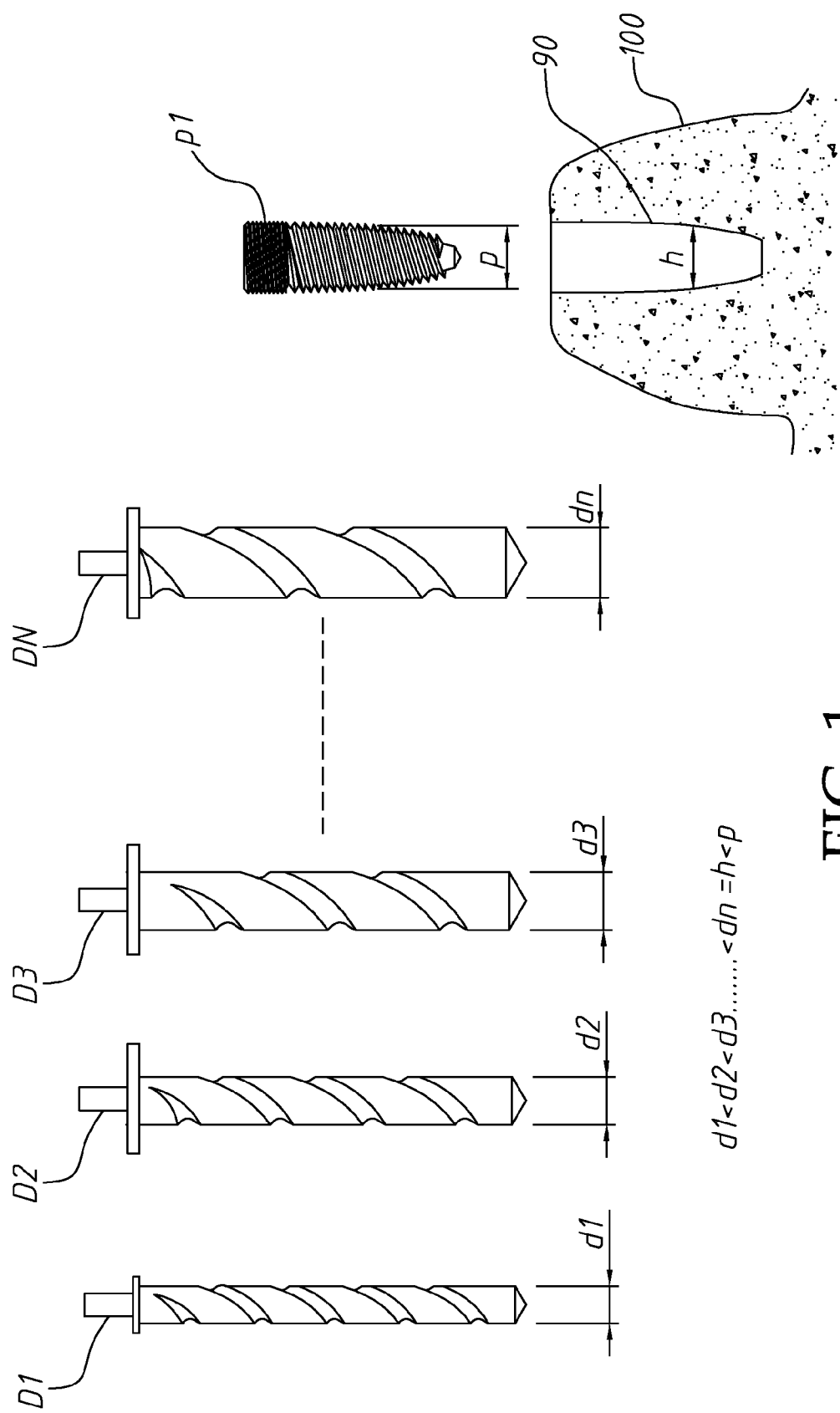
FIG. 1 illustrates a set of drill bits and a fixture for dental implant according to the prior art.
Figure 2:
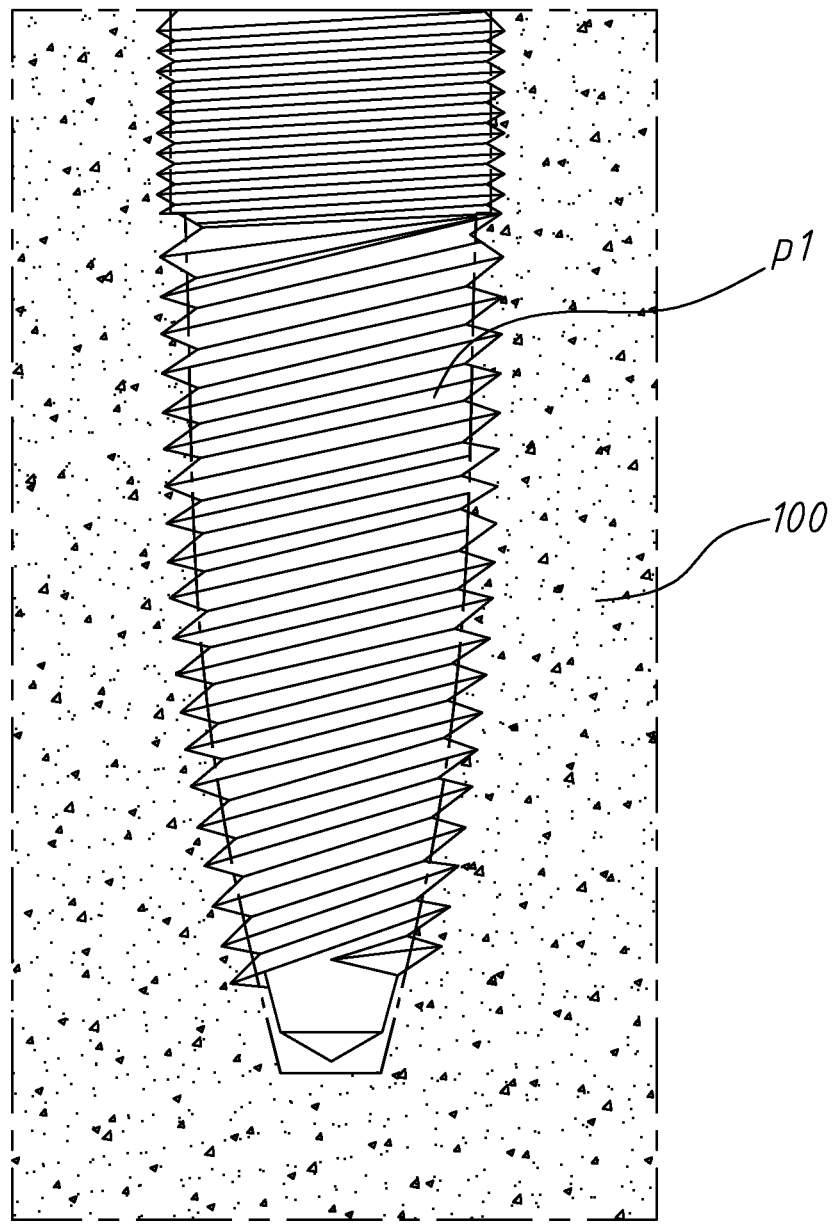
FIG. 2 is a schematic drawing illustrating a fixture embedded in a jawbone according to the prior art.
Figure 3:
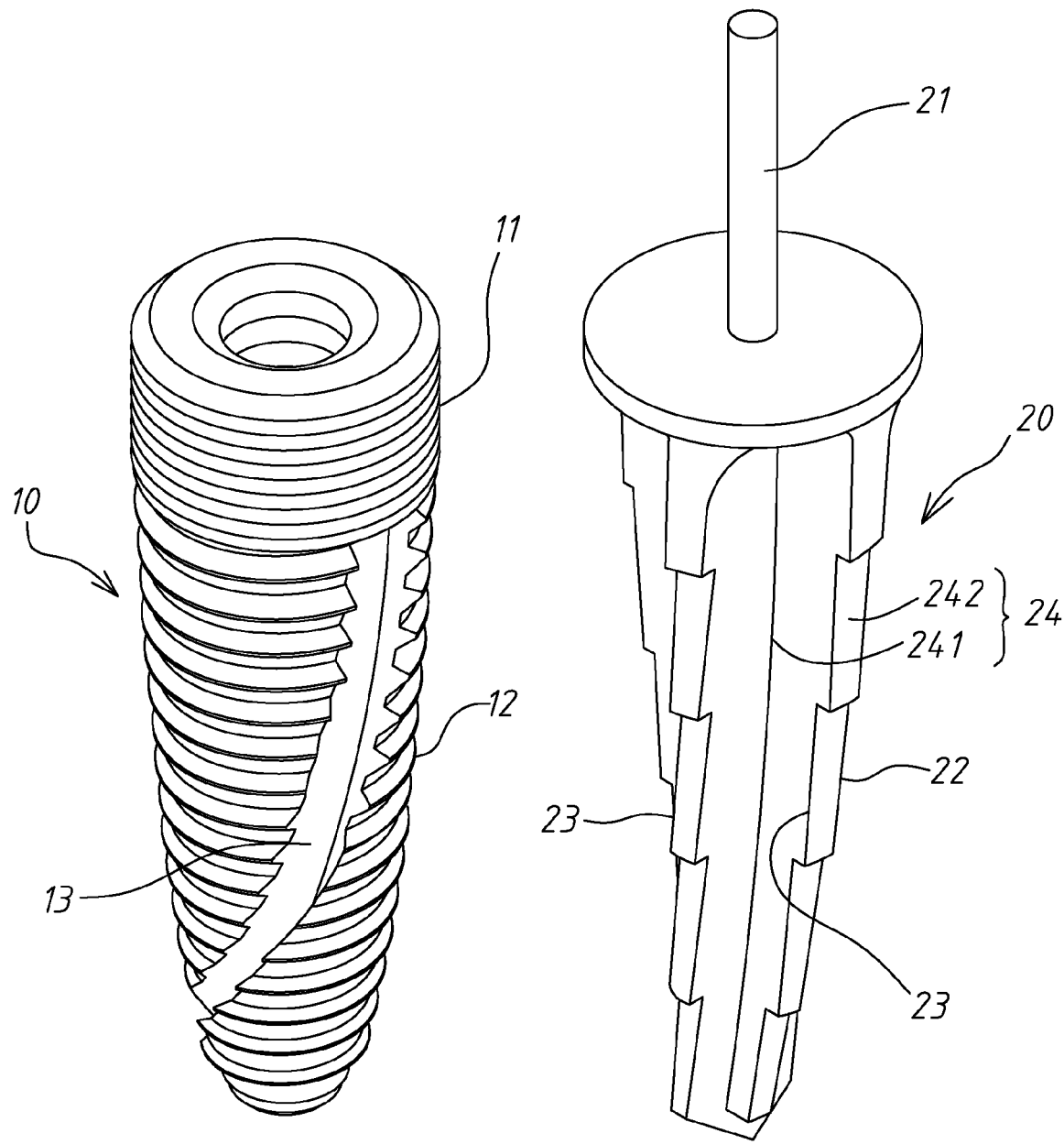
FIG. 3 is an elevational view of a quick dental implant kit in accordance with the present invention.

Referring to FIG. 3, a quick dental implant kit in accordance with the present invention is shown comprising a fixture 10 and a drill bit 20.

Figure 4:
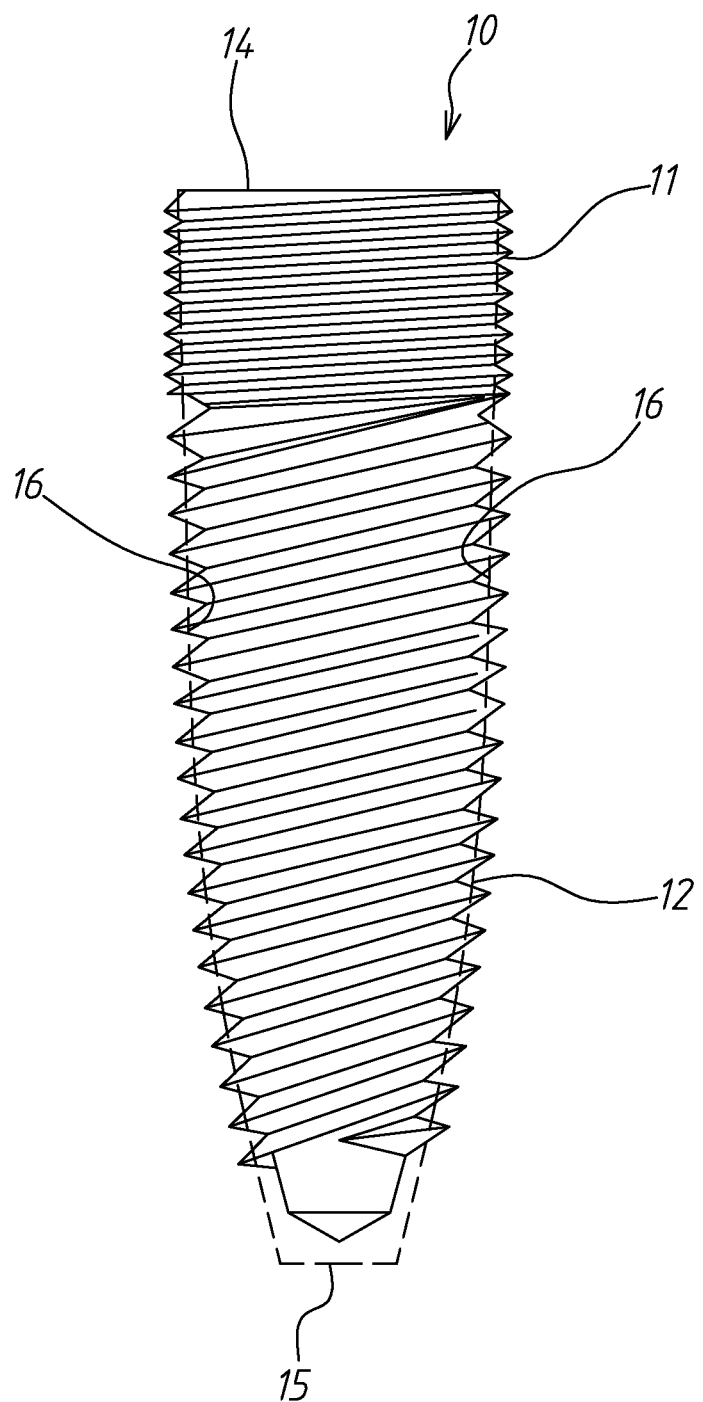
FIG. 4 is a schematic sectional view of the fixture of the quick dental implant kit in accordance with the present invention, illustrating the long arc-shaped contour of the fixture.

The fixture 10 comprises an upper fine thread portion 11, a lower coarse thread portion 12, and a plurality of spiral grooves 13 spirally extending from the top side of the lower coarse thread portion 12 toward the bottom side thereof across the threaded periphery. When driving the fixture 10 into the patient's jawbone, the spiral grooves 13 receive the cut tissue chips. As shown in FIG. 4, the fixture 10 has opposing top side 14 and bottom side 15 and a diameter gradually reducing from the top side 14 toward the bottom side 15, exhibiting a long arc-shaped contour 16 (see the imaginary line).

Figure 9:
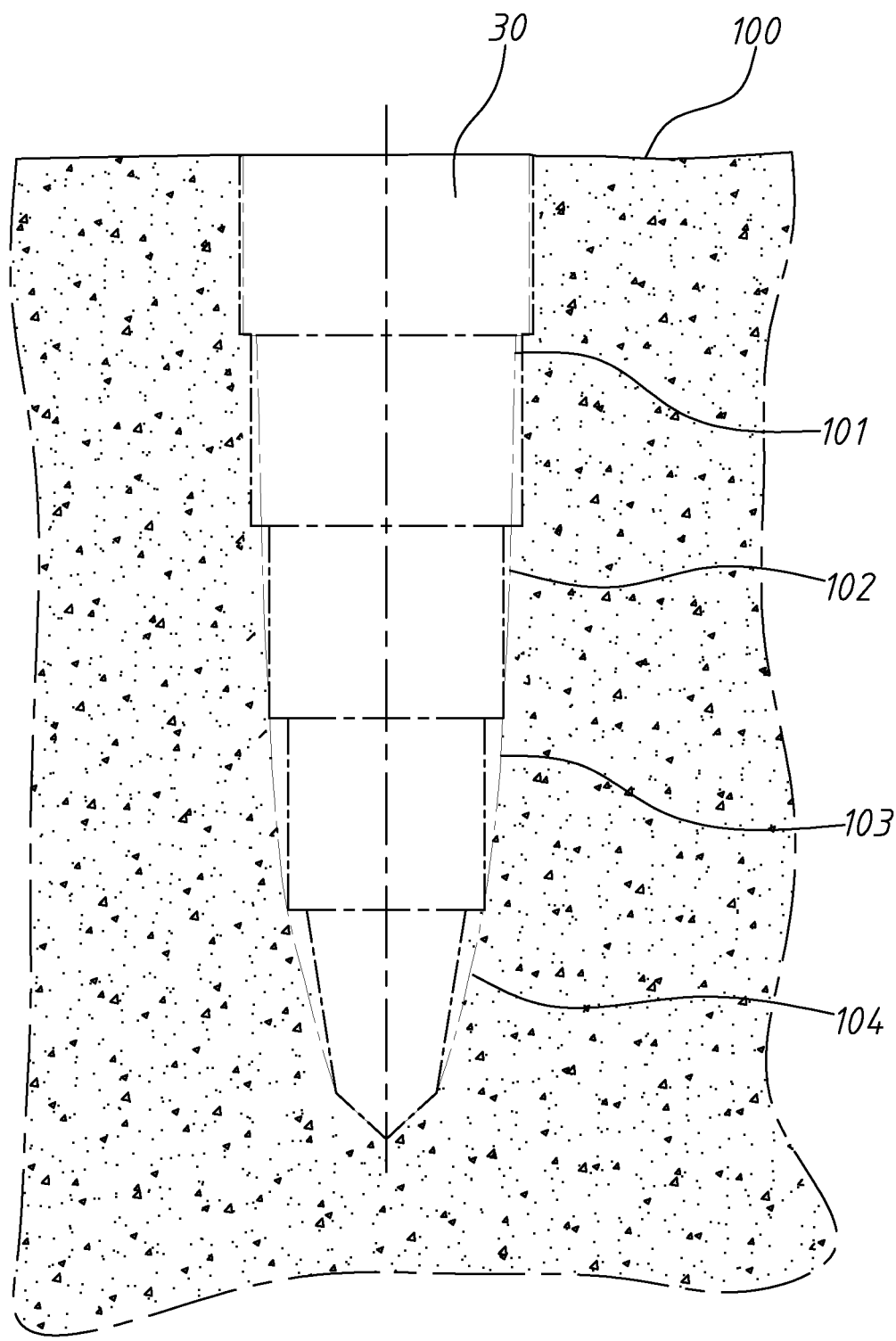
FIG. 9 is a schematic sectional view of a stepped hole made in the jawbone according to the present invention, wherein the imaginary line indicates the long arc-shaped contour of the fixture.

The drill bit 20 matches the fixture 10, comprising a shank 21 connectable to and rotatable by a dental handpiece 200 (see FIG. 6) and a stepped cutter body 22 formed integral with the bottom end of the shank 21 and defining a plurality of stepped cutting edges 23 for drilling a stepped hole 30 in the patient's jawbone 22 for the implant of the fixture 10, as shown in FIG. 9. The stepped cutter body 22 includes a plurality of cutter blades 24. Each cutter blade 24 has a root portion 241 and an edge portion 242, as shown in FIG. 3. The stepped cutting edges 23 are formed on the edge portion 242. The root portion 241 is connected to the root portions 241 of an adjacent cutter blade 24, whereby a V-shaped space is formed between two adjacent cutter blades 24. One of the cutter blades 24 is perpendicular to adjacent cutter blades 24.

Figure 5:
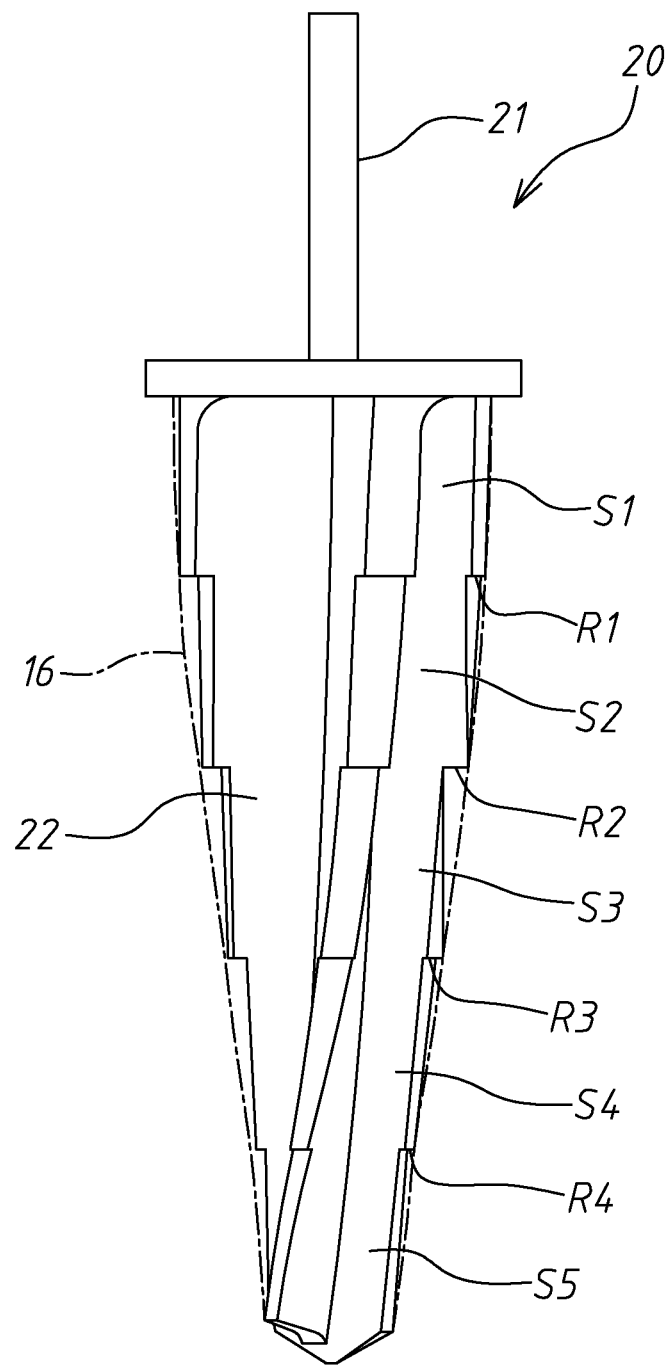
FIG. 5 is a schematic plain view of the drill bit of the quick dental implant kit in accordance with the present invention, illustrating the relationship between the configuration of the drill bit and the long arc-shaped contour of the fixture.

As shown in FIG. 5, the fixture 10 matches the drill bit 20 in shape. Each stepped cutting edge 23 of the stepped cutter body 22 of the drill bit 20 defines at least five steps S1~S5 and at least four risers R1~R4 that are alternatively connected in a longitudinal series to fit the long arc-shaped contour 16 of the fixture 10, i.e., the diameter of an upper one of the at least five steps S1~S5 is relatively greater than a lower one, and the long arc-shaped contour 16 of the fixture 10 extends over the risers R1~R4.

Figure 6:
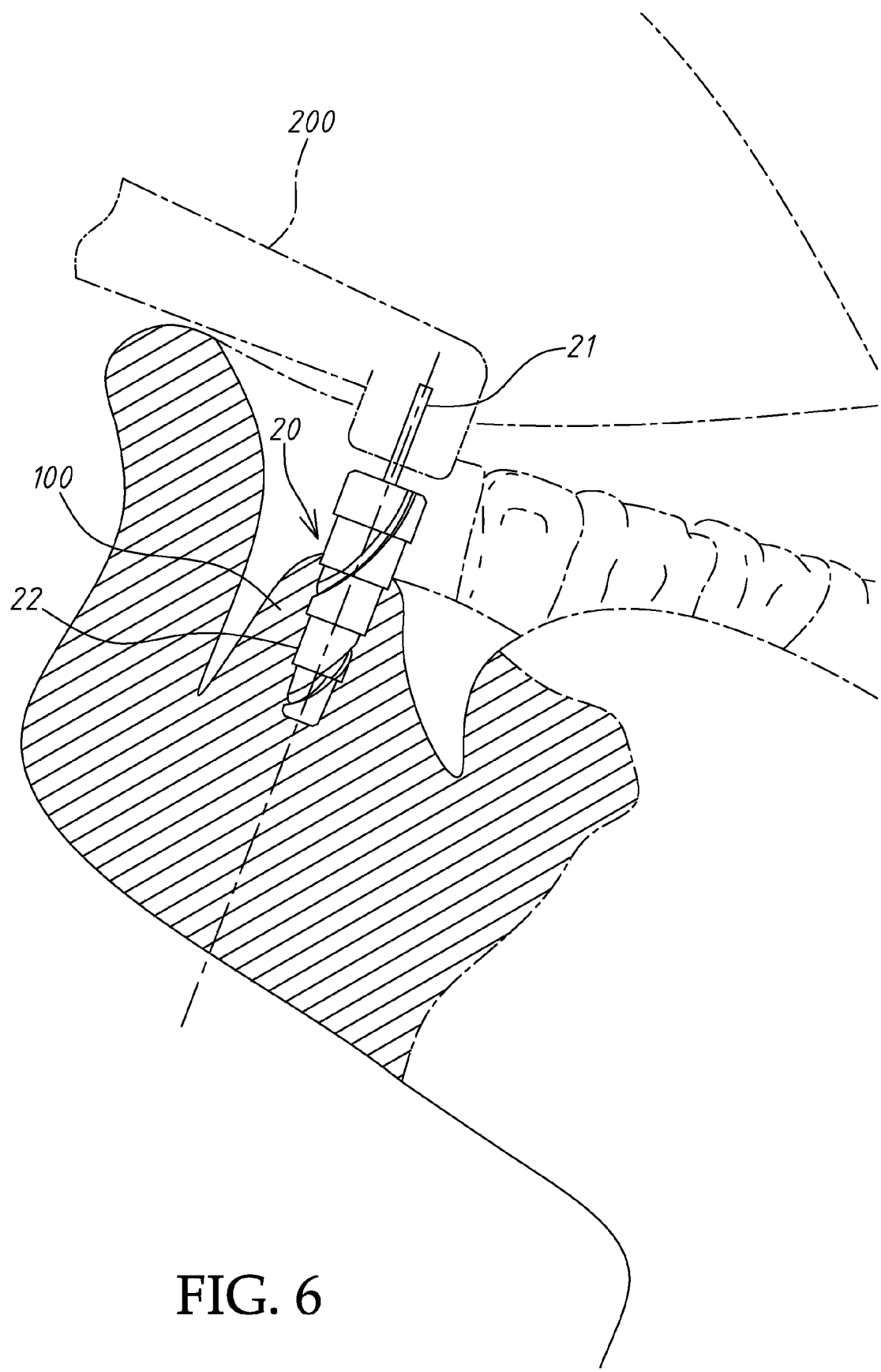
FIGS. 6~8 are schematic drawings of the present invention, illustrating the hole-drilling and fixture installation actions.
Figure 7:
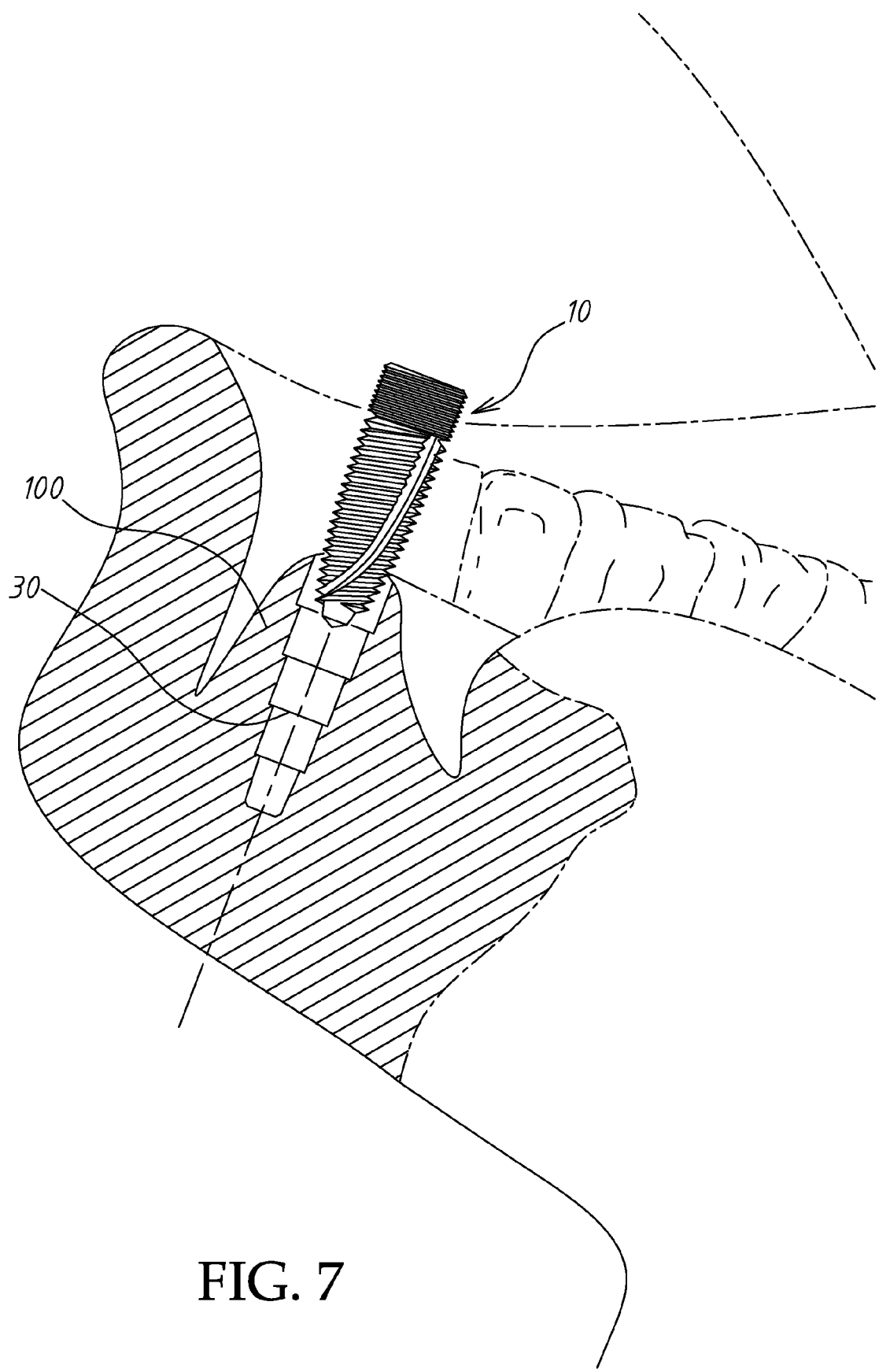
Figure 8:
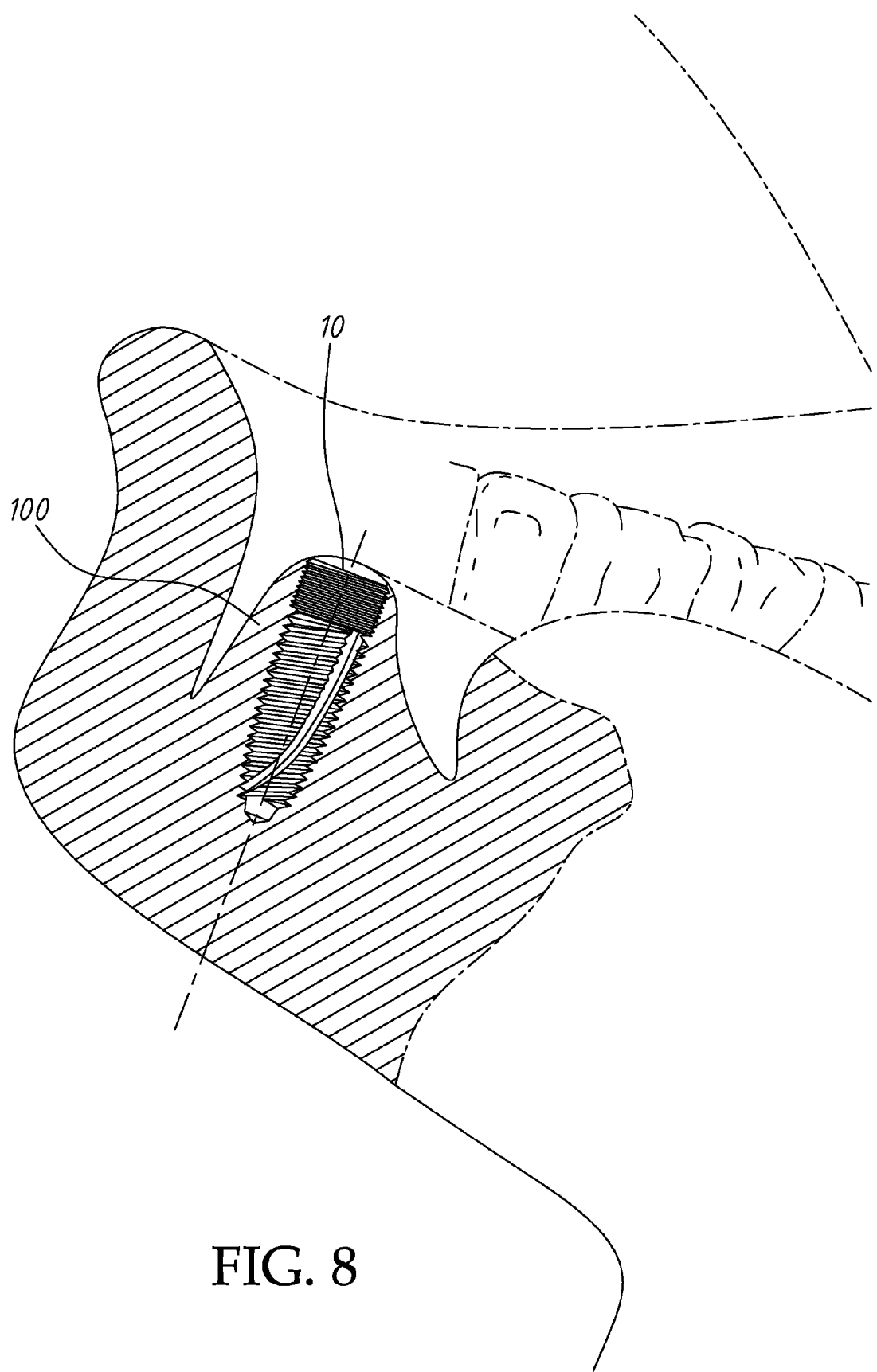

Referring to FIGS. 6-8, after removal of the damaged tooth from the patient's jawbone 100 and connection of the shank 21 of the drill bit 20 to the dental handpiece 200, the drill bit 20 can then be attached to the patient's jawbone 100 (see FIG. 6) and rotated by the dental handpiece 200 to drill a stepped hole 30 in the patient's jawbone 100 by the stepped cutting edges 23 (see FIG. 7 or FIG. 9). After formation of the stepped hole 30 in the patient's jawbone 100, the fixture 10 is attached to the stepped hole 30 as shown in FIG. 7, and then driven into the stepped hole 30 using a proper tool, enabling the fixture 10 to be completely embedded in the stepped hole 30, as shown in FIG. 8. After healing of the wound, an abutment is fastened to the fixture 10, and then a tooth crown is affixed to the abutment, finishing the dental implant procedure.

By means of using a drill bit 20 configured to fit the contour of the fixture 10 for drilling the desired stepped hole 30 in the patient's jawbone 100 instead of the prior art techniques of using a set of different diameters of drill bits D1~Dn, the invention greatly reduces the hole-drilling time, saves much the drill bit investment cost and shortens the treatment time.

Figure 10:
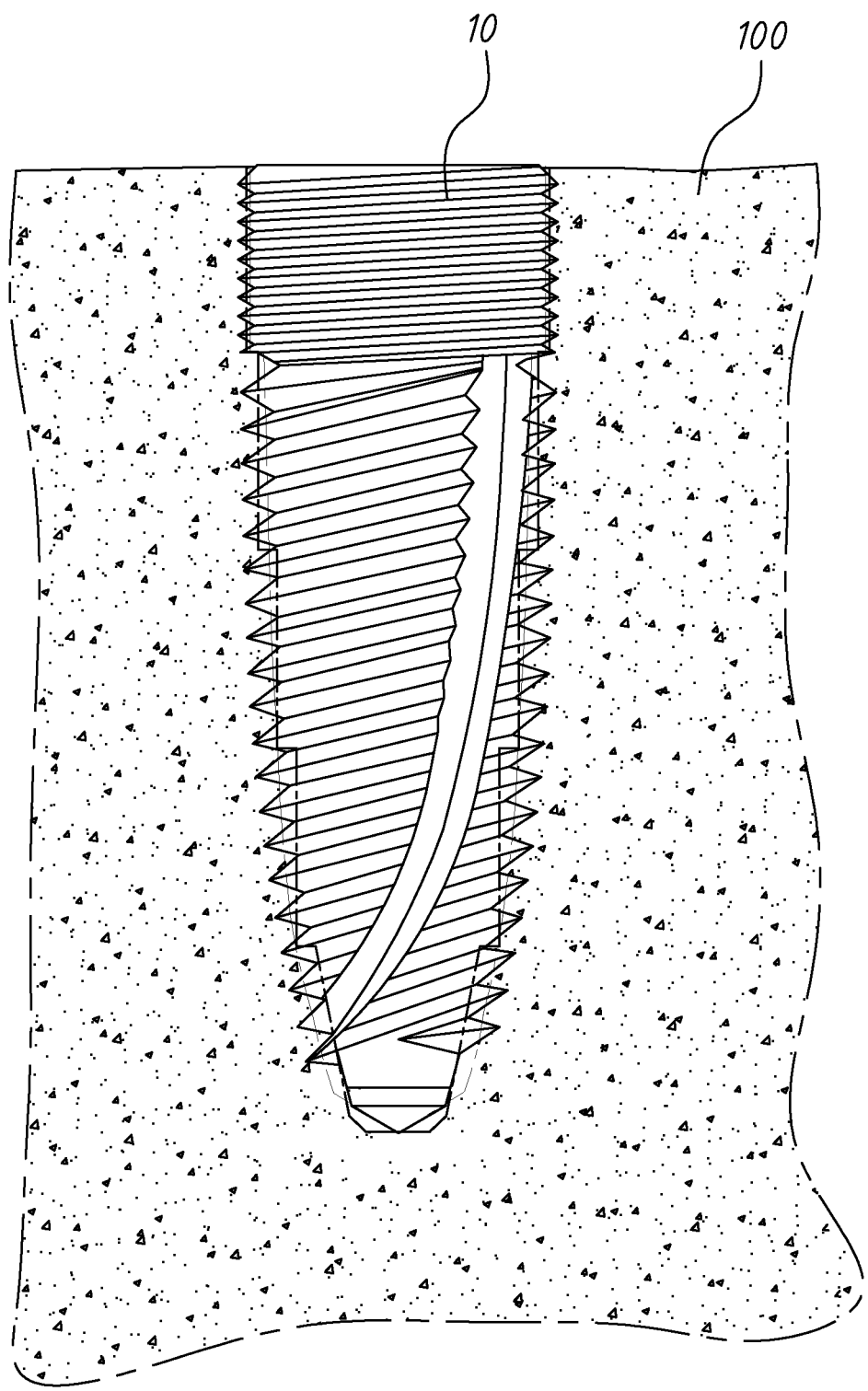
FIG. 10 is a schematic sectional view illustrating the fixture embedded in the stepped hole in the jawbone in accordance with the present invention.

Because each stepped cutting edge 23 of the stepped cutter body 22 of the drill bit 20 defines at least five steps S1~S5 and at least four risers R1~R4 and the long arc-shaped contour 16 of the fixture 10 extends over the risers R1~R4, tissues 101~104 in the stepped hole 30 corresponding to the clearances between the at least five steps S1~S5 of the stepped cutter body 22 of the drill bit 20 and the long arc-shaped contour 16 of the fixture 10 are preserved, as shown in FIG. 9. These preserved tissues 101~104 can be cut by the upper fine thread portion 11 or lower coarse thread portion 12 of the fixture 10 and can fall into the spiral grooves 13 upon installation of the fixture 10 in the stepped hole 30. After the fixture 10 has been completely embedded in the jawbone 100, as shown in FIG. 10, the tissues in the jawbone 100 are tightly abutted against the periphery of the fixture 10, and the cut tissue chips fill up the spiral grooves 13 for cell proliferation, eliminating a further bone powder filling process and saving much dental implant treatment time and labor.

It is to be understood that the number of steps of the stepped cutter body 22 of the drill bit 20 is not limited to 5, i.e., the number of steps of the stepped cutter body 22 of the drill bit 20 can be increased subject to actual requirements.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A quick dental implant kit, comprising:
    a fixture comprising an upper fine thread portion disposed at a top side thereof and a lower coarse thread portion disposed at a bottom side thereof, said fixture having a diameter gradually reducing in direction from the top side toward the bottom side and exhibiting a long arc-shaped contour; and
    a drill bit comprising a shank connectable to and rotatable by a dental handpiece and a stepped cutter body comprising a plurality of cutter blades extending outwardly from an axis of the drill bit and extending along a length of the stepped cutter body, wherein each cutter blade has a root portion and an edge portion and a plurality of stepped cutting edges formed on the edge portion for drilling a stepped hole in a jawbone of a patient for the implant of said fixture, each of said plurality of stepped cutting edges has at least five steps and at least four risers alternatively connected in a longitudinal series and extending along a length of the stepped cutter body to fit the long arc-shaped contour of said fixture, wherein the first step of the blades cutting edge is arranged to form a stepped portion of the hole that substantially matches the length of the fixture fine threaded portion when the fixture is installed, and the root portion of each cutter blade is directly connected to the root portion of an adjacent cutter blade of the plurality of cutter blades;
    wherein the plurality of cutter blades of the stepped cutter body includes four cutter blades, the stepped cutter body has a cross section having a shape of a cross, the stepped cutter body has the cross shaped cross section along the length thereof.

2. The quick dental implant kit as claimed in claim 1, wherein said fixture further comprises a plurality of spiral grooves located on the periphery and spirally extending from a top side of said lower coarse thread portion toward a bottom side thereof.

3. The quick dental implant kit as claimed in claim 1, wherein said stepped cutter body is integral with a bottom end of said shank.

4. The quick dental implant kit as claimed in claim 1, wherein one of the plurality of cutter blades is perpendicular to an adjacent cutter blade of the plurality of cutter blades.

5. The quick dental implant kit as claimed in claim 4, wherein the plurality of cutter blades are spiral along a longitudinal direction.

* * * * *